(12) United States Patent
Mahapatra

(10) Patent No.: US 10,639,100 B2
(45) Date of Patent: May 5, 2020

(54) DETERMINING ABLATION LOCATION USING PROBABILISTIC DECISION-MAKING

(71) Applicant: St. Jude Medical, Cardiology Division, Inc., St. Paul, MN (US)

(72) Inventor: Srijoy Mahapatra, Edina, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 184 days.

(21) Appl. No.: 15/892,994

(22) Filed: Feb. 9, 2018

(65) Prior Publication Data

US 2018/0228536 A1 Aug. 16, 2018

Related U.S. Application Data

(60) Provisional application No. 62/457,378, filed on Feb. 10, 2017.

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/742* (2013.01); *A61B 18/02* (2013.01);
(Continued)

(58) Field of Classification Search
CPC ..... A61B 18/1492; A61B 18/02; A61B 5/742; A61B 2018/00577; A61B 5/0422;
(Continued)

(56) References Cited

U.S. PATENT DOCUMENTS 6,233,476 B1 5/2001 Strommer et al.
6,498,944 B1 12/2002 Ben-Haim et al.
(Continued)

FOREIGN PATENT DOCUMENTS

WO 2012085750 A1 6/2012
WO 2012151301 A1 11/2012

OTHER PUBLICATIONS

International Search Report and Written Opinion for International Patent Application No. PCT/US2018/017596, dated Apr. 23, 2018, 12 pages.

*Primary Examiner* — Catherine M Voorhees
(74) *Attorney, Agent, or Firm* — Armstrong Teasdale LLP

(57) ABSTRACT

A method of determining a candidate ablation location using historical ablation data includes generating a database including a plurality of ablation records, and generating a set of probability parameters describing each ablation record. The method also includes developing an algorithm based upon the probability parameters for the ablation records. For a candidate ablation procedure, the method includes receiving patient parameters associated with a patient receiving the candidate ablation procedure, and determining at least one candidate condition associated with the patient and a respective probability associated with each candidate condition. The method further includes applying the algorithm to determine at least one candidate ablation location based upon the respective probabilities associated with the at least one candidate condition, and displaying the at least one candidate ablation location on a visual interface of a cardiac mapping system.

20 Claims, 3 Drawing Sheets

(51) Int. Cl.
- *A61B 34/10* (2016.01)
- *A61B 90/00* (2016.01)
- *G16H 50/50* (2018.01)
- *G16H 50/20* (2018.01)
- *A61N 7/02* (2006.01)
- *A61B 18/02* (2006.01)
- *A61B 18/12* (2006.01)
- *G16H 70/20* (2018.01)
- *G16H 40/63* (2018.01)
- *A61B 5/042* (2006.01)
- *A61B 18/00* (2006.01)
- *A61B 5/05* (2006.01)
- *A61N 7/00* (2006.01)
- *A61M 25/01* (2006.01)
- *A61B 34/00* (2016.01)
- *A61B 34/30* (2016.01)

(52) U.S. Cl.
CPC .............. *A61B 18/12* (2013.01); *A61B 34/10* (2016.02); *A61B 90/37* (2016.02); *A61N 7/02* (2013.01); *G16H 40/63* (2018.01); *G16H 50/20* (2018.01); *G16H 50/50* (2018.01); *G16H 70/20* (2018.01); *A61B 5/0422* (2013.01); *A61B 5/05* (2013.01); *A61B 5/4836* (2013.01); *A61B 34/30* (2016.02); *A61B 2018/00351* (2013.01); *A61B 2018/00357* (2013.01); *A61B 2018/00369* (2013.01); *A61B 2018/00375* (2013.01); *A61B 2018/00404* (2013.01); *A61B 2018/00577* (2013.01); *A61B 2018/00648* (2013.01); *A61B 2018/00791* (2013.01); *A61B 2018/00839* (2013.01); *A61B 2018/0262* (2013.01); *A61B 2034/105* (2016.02); *A61B 2034/107* (2016.02); *A61B 2034/256* (2016.02); *A61B 2034/258* (2016.02); *A61B 2090/364* (2016.02); *A61B 2090/365* (2016.02); *A61M 25/0147* (2013.01); *A61N 2007/003* (2013.01)

(58) Field of Classification Search
CPC . A61B 18/12; A61B 5/4836; A61B 2034/258; A61B 2034/256; A61B 2090/365; A61B 2034/107; A61B 2034/105; A61B 34/30; A61B 2090/364; A61B 90/37; A61B 34/10; A61N 7/02; G16H 50/20; G16H 70/20; G16H 50/50
See application file for complete search history.

(56) References Cited

U.S. PATENT DOCUMENTS

| | | | |
|---|---|---|---|
| 6,690,963 B2 | 2/2004 | Ben-Haim et al. | |
| 6,767,325 B2 | 7/2004 | Iliff | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 8,688,469 B2 | 4/2014 | Ziegler et al. | |
| 2006/0111933 A1 | 5/2006 | Wheeler | |
| 2013/0006131 A1* | 1/2013 | Narayan | A61B 5/042 600/508 |
| 2018/0221075 A1* | 8/2018 | Warner | A61B 5/4848 |

* cited by examiner

DETERMINING ABLATION LOCATION USING PROBABILISTIC DECISION-MAKING

CROSS REFERENCE TO RELATED APPLICATIONS

This application claims priority to provisional application Ser. No. 62/457,378, filed Feb. 10, 2017 which is incorporated herein by reference in its entirety.

FIELD OF THE DISCLOSURE

The present disclosure relates generally to cardiac mapping systems. In particular, in many embodiments, the present disclosure relates to cardiac mapping systems and methods for use in performing probabilistic decision-making during an electrophysiological (EP) procedure.

BACKGROUND

Atrial arrhythmias are conditions causing an irregular heartbeat that can result in blood clots, stroke, heart failure, and other cardiac complications. It is believed that the primary cause of atrial arrhythmia is stray electrical signals within the left or right atrium of the heart. It is generally known that ablation therapy may be used to treat atrial arrhythmias, including atrial fibrillation (AF) and other conditions. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct atrial arrhythmia. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

Determining an ablation location within a patient's heart may be relatively difficult. Different ablation locations are associated with different cardiac conditions, and each patient's heart is different. Although at least some solutions have been posed to identify ablation locations using software, it has been observed that many practitioners do not always follow software recommendations, instead choosing to rely on clinical knowledge in determining where to ablate.

BRIEF SUMMARY

The present disclosure generally relates to cardiac mapping systems and methods of using the same. In many embodiments, the cardiac mapping system incorporates a probabilistic algorithm to identify candidate ablation locations. The algorithm is developed based upon ablation procedures that have been completed successfully, enabling non-expert practitioners to leverage the clinical knowledge of expert practitioners in determining ablation locations. Other embodiments and descriptions of the present disclosure are set forth below.

In one embodiment, the present disclosure is directed to a method of determining a candidate ablation location using historical ablation data. The method includes generating a database including a plurality of ablation records. Each ablation record of the plurality of ablation records is associated with a corresponding ablation procedure. The method also includes generating a set of probability parameters describing each ablation record of the plurality of ablation records, and developing an algorithm based upon the sets of probability parameters for the plurality of ablation records. The method further includes, for a candidate ablation procedure, receiving a plurality of patient parameters associated with a patient receiving the candidate ablation procedure, and determining at least one candidate condition associated with the patient and a respective probability associated with each candidate condition. The method also includes applying the algorithm to determine at least one candidate ablation location based upon the respective probabilities associated with the at least one candidate condition, and displaying the at least one candidate ablation location on a visual interface of a cardiac mapping system.

In another embodiment, the present disclosure is directed to a cardiac mapping system including a database, a display device, and a processing apparatus in communication with the database and the display device. The processing apparatus is configured to populate the database with a plurality of ablation records. Each ablation record of the plurality of ablation records is associated with a corresponding ablation procedure. The processing apparatus is also configured to generate a set of probability parameters describing each ablation record of the plurality of ablation records, and develop an algorithm based upon the sets of probability parameters for the plurality of ablation records. The processing apparatus is further configured to, for a candidate ablation procedure, receive a plurality of patient parameters associated with a patient receiving the candidate ablation procedure, and determine at least one candidate condition associated with the patient and a respective probability associated with each candidate condition. The processing apparatus is also configured to apply the algorithm to determine at least one candidate ablation location based upon the respective probabilities associated with the at least one candidate condition, and display the at least one candidate ablation location on the display device.

In another embodiment, the present disclosure is directed to at least one non-transitory computer-readable storage medium having computer-executable instructions embodied thereon. When executed by at least one processor in communication with a database and a display device, the computer-executable instructions cause the at least one processor to populate the database with a plurality of ablation records, each ablation record of the plurality of ablation records associated with a corresponding ablation procedure. The computer-executable instructions also cause the at least one processor to generate a set of probability parameters describing each ablation record of the plurality of ablation records, and develop an algorithm based upon the sets of probability parameters for the plurality of ablation records. The computer-executable instructions also cause the at least one processor to, for a candidate ablation procedure, receive a plurality of patient parameters associated with a patient receiving the candidate ablation procedure, and determine at least one candidate condition associated with the patient and a respective probability associated with each candidate condition. The computer-executable instructions also cause the at least one processor to apply the algorithm to determine at least one candidate ablation location based upon the respective probabilities associated with the at least one candidate condition, and display the at least one candidate ablation location on the display device.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION

The present disclosure relates generally to cardiac mapping systems. In particular, in many embodiments, the present disclosure relates to cardiac mapping systems and methods for use in performing probabilistic decision-making during an electrophysiological (EP) procedure. The disclosed embodiments may improve patient outcome in EP procedures performed by non-expert physicians and may improve consistency in the performance and outcomes of EP procedures across physicians. It is contemplated, however, that the described features and methods of the present disclosure as described herein may be incorporated into any number of systems as would be appreciated by one of ordinary skill in the art based on the disclosure herein.

Figure 1:
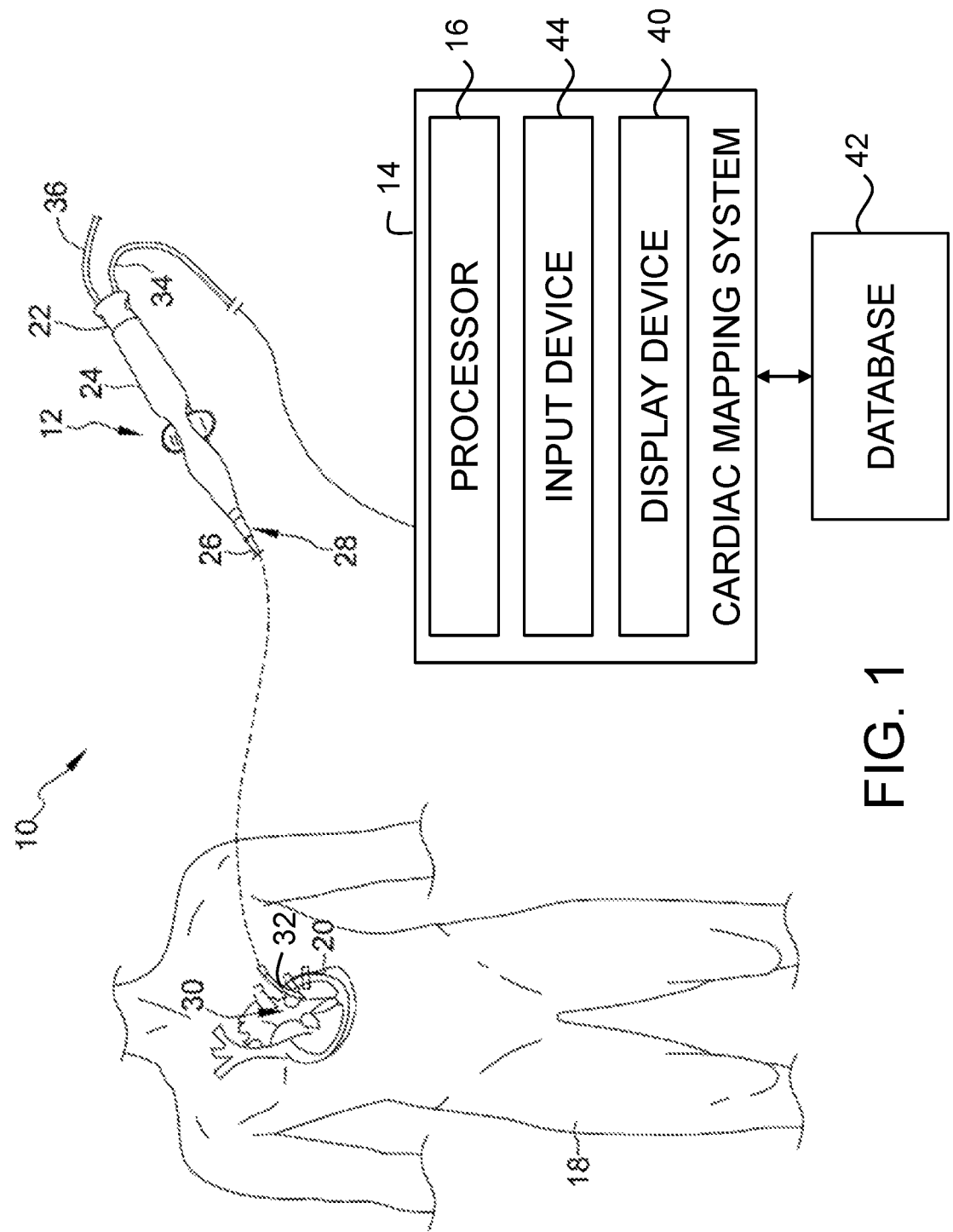
FIG. 1 is a schematic and block diagram view of an ablation system including a cardiac mapping system incorporating embodiments for probabilistic ablation location identification.

Referring now to the drawings, FIG. 1 is a diagrammatic and block diagram view of an ablation system 10 for performing EP procedures, specifically cardiac ablation procedures. Ablation system 10 may be used for any type of ablation therapy, including radiofrequency (RF) ablation, cryoablation, ultrasound ablation, electroporation, and/or any other ablation procedure. In general, ablation system 10 includes, among other components, a catheter 12 and a cardiac mapping system 14. Catheter 12 includes an ablation and/or mapping catheter 12, and cardiac mapping system 14 includes, in part, a processing apparatus 16. Processing apparatus 16 may take the form of an electronic control unit, for example, that is configured to generate a three-dimensional model of the heart 20 within a patient's body 18, using data collected by catheter 12.

As illustrated in FIG. 1, catheter 12 is configured to be inserted into a patient's body 18, and more particularly, into the patient's heart 20. Catheter 12 may include a cable connector or interface 22, a handle 24, and a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient). Catheter 12 may include one or more sensors 32 mounted in or on shaft 26 of catheter 12. In this embodiment, sensors 32 are disposed at or near distal end 30 of shaft 26. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to cardiac mapping system 14 and/or other components of ablation system 10 (e.g., an ablation generator, irrigation source, etc.). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiment, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by, for example, cardiac mapping system 14, in the construction of a three-dimensional model of the patient's heart 20.

Cardiac mapping system 14 is configured to construct a three-dimensional model of structures within heart 20 using, in part, location data collected by catheter 12. More particularly, processing apparatus 16 of cardiac mapping system 14 is configured to acquire location data points collected by sensor(s) 32 and to then use those location data points in the construction or generation of a model of the structure(s) to which the location data points correspond. Cardiac mapping system 14 may comprise an electric field-based system, such as, for example, the EnSite™ NavX™ system commercially available from Abbott Laboratories, or an electric impedance- and magnetic field-based system such as the EnSite™ Precision™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, cardiac mapping system 14 may comprise other types of systems, such as, for example and without limitation: a magnetic-field based system such as a system as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems. Cardiac mapping system 14 displays the generated cardiac models on a display device 40. Display device 40 may include a monitor (e.g., an output-only display device) or a touchscreen display (e.g., an input-output display device).

Cardiac mapping system 14 further includes and/or is in communication with a database 42. Database 42 includes a plurality of records of historical (i.e., already-performed) ablation procedures, or "ablation records." The ablation records are generated and stored in database 42 manually and/or automatically. In some embodiments, a subset of the plurality of ablation records are associated with ablation procedures performed and described in published literature, such as medical journals, scholarly articles, and the like. In some embodiments, a subset of the plurality of ablation records are associated with ablation procedures performed and observed/recorded by one or more medical professionals, such as medical directors. In some embodiments, a subset of the plurality of ablation records are associated with ablation procedures performed by expert physicians and recorded in database 42. A physician may be considered an "expert" when they meet one or more expert criteria, including, for example, a threshold number of EP procedures performed, a threshold number of successful EP procedures performed (e.g., EP procedures having a successful patient outcome, such as elimination of atrial fibrillation (AF)), a threshold percentage of successful EP procedures performed, a number of publications attributable to the physician, and/or any other expert criteria. Expert criteria may shift over time, as new physicians become experts and/or more EP procedures are performed.

Each ablation record includes data elements associated with the patient, such as age, condition, sex, weight, and/or additional data. Each ablation record also includes data elements associated with the EP condition, such as one or more type(s) of arrhythmia experienced (e.g., AF, ventricular tachycardia (VT), ventricular fibrillation (VF) atrial tachycardia (AT)), symptoms, and/or the type of EP condition being treated with an ablation procedure. Each ablation record also includes data elements associated with the ablation procedure, including what type of procedure was performed, any ablation locations at which ablation was performed, and an indication of outcome (e.g., successful, unsuccessful, partially successful). In some embodiments, ablation records include data elements identifying the physician that performed the EP procedure and/or whether the physician is an expert physician.

Processing apparatus 16 (and/or another processing component in communication with database 42) is configured to generate a set of probability parameters describing each ablation record of the plurality of ablation records. The probability parameters are associated with the different types of cases/conditions, as well as with the different types of patients. The probability parameters may be characterized as "pre-test" parameters or filtering criteria for developing an algorithm, as described further herein. Processing apparatus 16 stores the probability parameters in database 42 and/or in an additional memory component (not shown) in cardiac mapping system 14.

Processing apparatus 16 also develops an algorithm based upon the sets of probability parameters for the plurality of ablation records, stored in database 42. The algorithm is configured to output a probability that ablating in a particular ablation location will be successful, based on the historical ablation records in database 42 and associated probability parameters. More specifically, the algorithm is employed for each candidate (i.e., yet to be performed) ablation procedure. Generally, the algorithm may include a regression analysis configured to process the ablation records and identify probability parameters (or variables or filtering criteria) that tend to have some correlation with particular outcomes. In other words, the algorithm is developed without identifying a particular parameter or criterion that correlates with a particular condition or outcome. Rather, the algorithm employs a regression analysis to identify and then incorporate the parameters or criteria that correlate with condition or outcome to direct candidate ablation locations in later ablation procedures.

Processing apparatus 16 generates a table or matrix of candidate conditions and corresponding candidate ablation locations to be associated with each type of condition. More specifically, processing apparatus 16 matches or associates stored probability parameters with corresponding candidate conditions. For example, certain probability parameters are matched to an AF condition for those probability parameters having a strong correlation with that AF condition. Within the table or matrix, processing apparatus 16 applies probability adjusters to candidate conditions, the probability adjusters corresponding to the correlation between certain probability parameters and certain conditions. If no correlation is known, in the example embodiment, processing apparatus 16 applies a probability adjuster of "1" to a candidate condition. In the example embodiment, processing apparatus 16 generates a "probabilities tree" using the table and the stored probabilities. More specifically, processing apparatus 16 applies the Bayes theorem to the table to generate a probabilities tree of candidate conditions associated with the candidate ablation procedure:

$$P(H|E) = \frac{P(H)*P(E|H)}{P(E)},$$

where P(H) represents the prior probability that a hypothesis 'H' is true, P(E|H) represents the likelihood of evidence 'E' if hypothesis 'H' is true, and P(E) represents the prior probability that the evidence 'E' is true. In other words, P(H) and P(E) represents respective probabilities of observing hypothesis 'H' and observing evidence 'E' without regard to one another, and P(E|H) represents a conditional probability of observing hypothesis 'H' given that evidence 'E' is true. The outcome P(H|E) represents the probabilities tree, or the final probability of hypothesis 'H' given the evidence 'E.'

A simplified probabilities tree is illustrated below. Taking the following example values for successful ablation procedures:

|  | Candidate condition A | Candidate condition B | Candidate condition C |
| --- | --- | --- | --- |
| Ablation Location 1 | 10% | 5% | 2% |
| Not Ablation Location 1 | 90% | 95% | 98% |

Assuming, of 500 cases, 100 cases (20%) experienced Candidate condition A, 200 cases (40%) experienced Candidate condition B, and 200 cases (40%) experienced Candidate condition C:

$P(A) = 0.2 \rightarrow P(AL1|A) = 0.1 \quad P(A) * P(AL1|A) = 0.2 * 0.1 = 0.02$ $P(AL1'|A) = 0.9 \quad P(A) * P(AL1'|A) = 0.2 * 0.9 = 0.18$ $P(B) = 0.4 \rightarrow P(AL1|B) = 0.05 \quad P(B) * P(AL1|B) = 0.4 * 0.05 = 0.02$ $P(AL1'|B) = 0.95 \quad P(B) * P(AL1'|B) = 0.4 * 0.95 = 0.38$ $P(C) = 0.4 \rightarrow P(AL1|C) = 0.02 \quad P(C) * P(AL1|C) = 0.4 * 0.02 = 0.008$ $P(AL1'|C) = 0.98 \quad P(C) * P(AL1'|C) = 0.4 * 0.98 = 0.392$ The probability of successfully ablating in ablation location 1 for any of candidate conditions A, B, and C, is 0.048.

In a first example, a 45-year-old patient presents with a paroxysmal AF. The patient has no history of alcohol use, no hypertension/high blood pressure, no diabetes, and a normal left atrium size. A "pre-test" probability prediction (e.g., a prediction based upon the literature associated with paroxysmal AF and/or expert opinion) is that there is a 90% chance that pulmonary vein ablation would be a successful treatment. Ablation in the location of pulmonary vein is chosen as the optimal treatment strategy. The patient undergoes cardiac mapping, during which a low voltage is seen on the posterior cardiac wall, and a rotor is seen on the posterior cardiac wall near a scar. The "post-test" probability (e.g., the probability based upon the actual characterization of the patient) indicates that pulmonary vein ablation has a 50% chance of being successful, and posterior wall ablation has a 50% chance of being successful. In this case, a posterior wall ablation location may be chosen, and a new data record with patient and ablation procedure variables will be added to the database to update the algorithm.

In a second example, a 70-year-old patient presents with persistent AF. The patient has hypertension/high blood pressure and diabetes, as well as a left atrium size of 55. A "pre-test" probability prediction is that there is a 50% probability that pulmonary vein ablation would be a successful treatment, a 25% probability that posterior wall ablation would be successful, a 20% probability that left atrial appendage ablation would be successful, and a 5% probability that a superior vena cava ablation would be successful. Ablation in the location of the posterior wall, as well as possible left atrial appendage clipping, is chosen as the optimal treatment strategy. The patient undergoes cardiac mapping with isoproterenol, during which a driver from the superior vena cava is seen, and no scar in the left atrium is seen. The "post-test" probability indicates that ablation in the location of the pulmonary vein has a 50% chance of being successful, and ablation in the location of the superior vena cava has a 50% chance of being successful. In this case, a pulmonary vein and superior vena cava isolation (no posterior wall ablation) may be chosen for treatment, and a new data record with patient and ablation procedure variables will be added to the database to update the algorithm.

Processing apparatus 16 employs the above-described probabilistic analysis to identify and output candidate ablation locations on display device 40 during each candidate ablation procedure. Data specific to the candidate ablation procedure is input to cardiac mapping system 14. Specifically, in the example embodiment, an input device 44 is used to input patient- and case-specific data associated with the candidate ablation procedure. Input device 44 may include, for example, a keyboard, mouse, touch screen interface, and/or any other suitable input device. Such information as a patient age, a patient gender, a patient weight, one or more known patient conditions, and/or one or more known patient symptoms are input using input device 44.

In some embodiments, one or more patient conditions and/or symptoms are determined using diagnostic techniques. One or more diagnostic techniques may be performed using ablation system 10, such as complex fractionated atrial electrogram (CFAE), local activation time (LAT), direction of activation, curl/divergence analysis, phase mapping, dominant frequency mapping, and/or any other known diagnostic technique. Based on one or more diagnosed patient conditions ("candidate conditions"), processing apparatus 16 applies the algorithm described above to identify one or more candidate ablation locations and the corresponding probability that ablating in each ablation location will be successful (i.e., lead to a successful outcome for the patient). The algorithm factors in patient- and case-specific data to identify and display one or more candidate ablation locations that are most likely to provide successful patient outcomes if ablation is performed at those candidate ablation locations. Processing apparatus 16 may therefore provide probabilistic indicators to a physician to aid in decision-making during an EP procedure.

Figure 2:
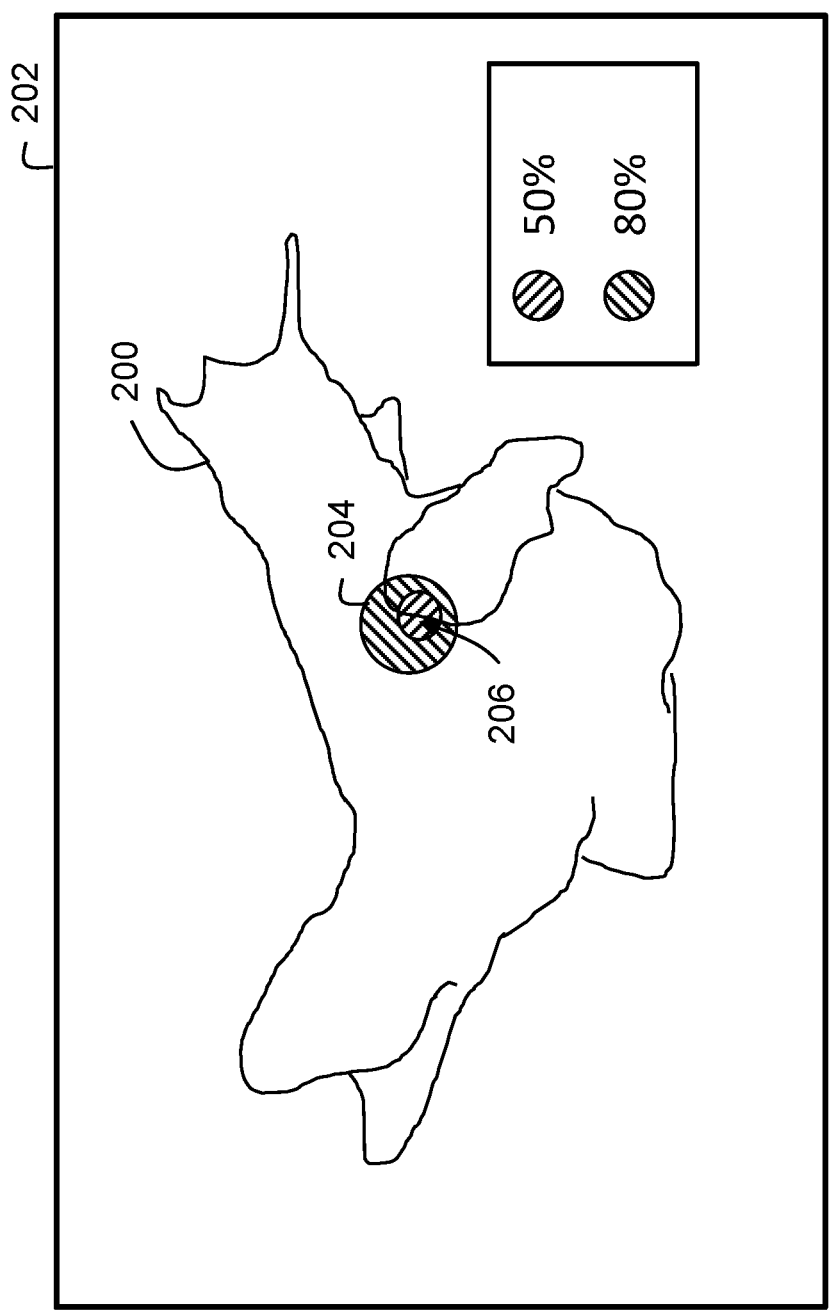
FIG. 2 illustrates an example visual interface of the cardiac mapping system shown in FIG. 1 including one or more visual indicators of a candidate ablation location.

In the example embodiment, processing apparatus 16 causes display of the identified candidate ablation locations on display device 40. More specifically, processing apparatus 16 causes display of the identified candidate ablation locations with respect to the three-dimensional model of the patient's heart 20, providing visual indicators to the physician of where within the model (and therefore where within the heart 20) to ablate. In some embodiments, processing apparatus 16 displays the identified candidate ablation locations using a color map, a probability map, or similar visual indicator overlaid on an existing three-dimensional model. For example, FIG. 2 illustrates one example cardiac model 200 displayed on a visual interface 202 of display device 40. Visual indicators 204 are displayed as overlays on cardiac model 200 to identify a candidate ablation location 206 to a physician performing an EP procedure. Additionally or alternatively, visual indicators such as arrows, icons, labels, highlighting, bolding, shading, annotations, and/or any other visual indicator are further displayed on visual interface 202 of display device 40.

Additionally, after each EP procedure is completed, input device 44 (and/or any other input device in communication with database 42) is used to input details from the EP procedure into database 42 as an additional ablation record.

In this manner, database 42 and the probabilistic algorithm are iteratively developed and refined in response to EP procedures initially performed using the algorithm. In some embodiments, a threshold amount of time between completion of the EP procedure and entry into database 42 is allowed to pass, such that accurate outcomes of the EP procedure may be determined.

Figure 3:
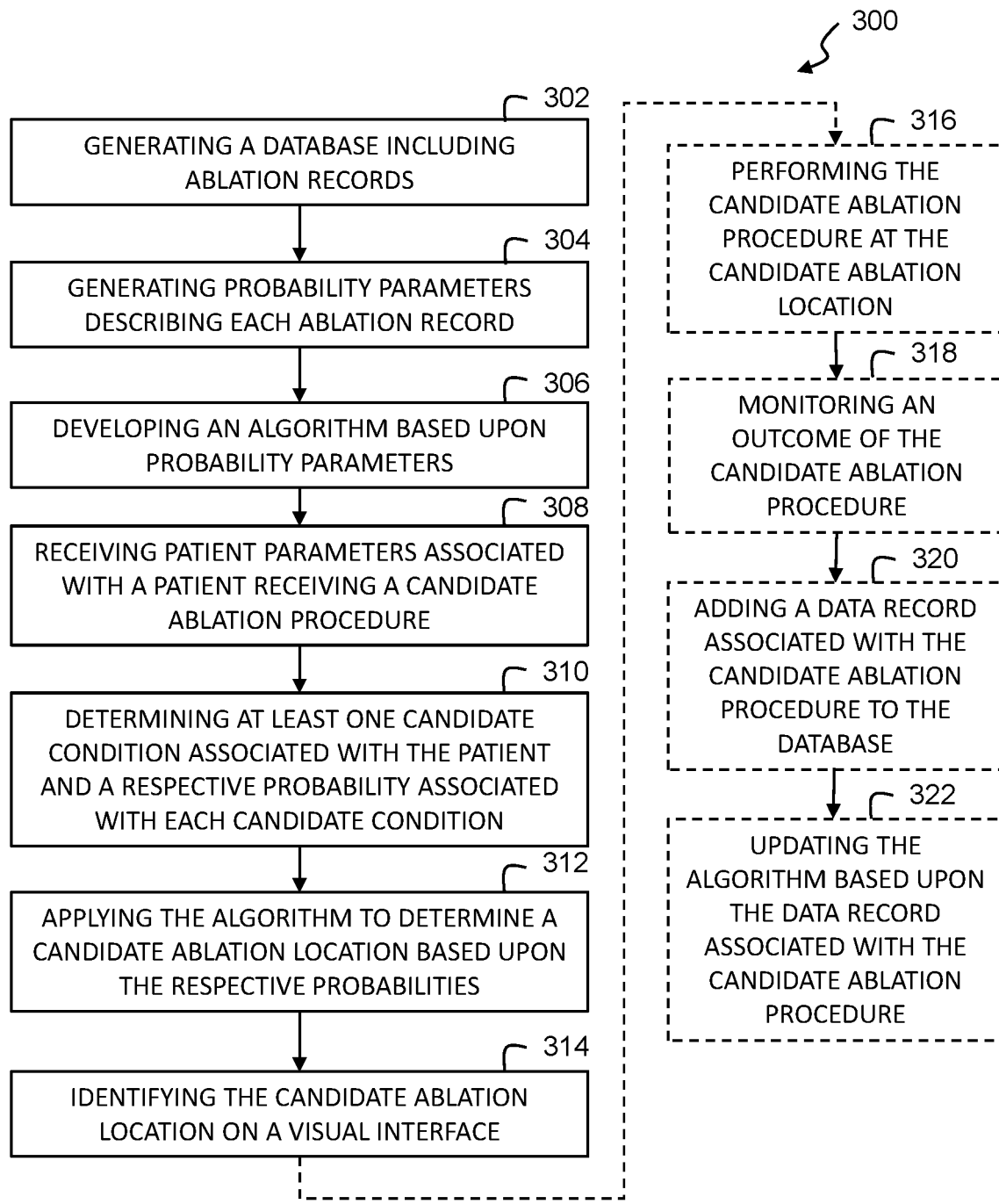
FIG. 3 is a flowchart illustrated an example method for determining a candidate ablation location using probabilistic analysis of historical ablation data.

FIG. 3 is a flowchart of a method 300 of determining a candidate ablation location using historical ablation data. In the example embodiment, method 300 is performed using cardiac mapping system 14 (shown in FIG. 1).

Method 300 includes generating 302 a database (e.g., database 42, shown in FIG. 1) including a plurality of ablation records. Each ablation record of the plurality of ablation records is associated with a corresponding ablation procedure that has already been performed. In some embodiments, generating 302 includes generating a subset of the plurality of ablation records based upon published data of the corresponding ablation procedures. In some embodiments, generating 302 includes generating a subset of the plurality of ablation records based upon historical ablation procedures performed by one or more ablation practitioners who meet at least one expert criterion. In some embodiments, each ablation record identifies a condition and an ablation location associated with the corresponding ablation procedure. Method 300 also includes generating 304 a set of probability parameters describing each ablation record of the plurality of ablation records.

Method 300 further includes developing 306 an algorithm based upon the sets of probability parameters for the plurality of ablation records. For each candidate ablation procedure to be performed using ablation system 10 (shown in FIG. 1), method 300 also includes receiving 308 a plurality of patient parameters associated with a patient receiving the candidate ablation procedure (e.g., using input device 44, shown in FIG. 1) and determining 310 at least one candidate condition associated with the patient and a respective probability associated with each candidate condition. In some embodiments, determining 310 including using one or more diagnostic techniques to identifying candidate conditions.

Method 300 includes applying 312 the algorithm to determine at least one candidate ablation location based upon the respective probabilities associated with the at least one candidate condition, and displaying 314 the at least one candidate ablation location on a visual interface (e.g., visual interface 202, shown in FIG. 2) of an ablation system. In some embodiments, displaying 314 includes adding at least one visual indicator of a corresponding ablation location onto an ablation map of the ablation system, such as cardiac model 200 (shown in FIG. 2). More particularly, adding a visual indicator may include adding at least one color to the ablation map to form a color map or probability map identifying the at least one candidate ablation location. Additionally or alternatively, adding a visual indicator may include adding at least one probability indicator to a respective location on the ablation map corresponding to the at least one candidate ablation location. In some embodiments, displaying 314 includes associating each at least one candidate ablation location with a corresponding point on an ablation map of the ablation system, and adding at least one visual indicator onto each point on the ablation map associated with each at least one candidate ablation location.

Method 300 may include additional, fewer, and/or alternative steps. For example, in some embodiments, method 300 further includes performing 316 the candidate ablation procedure at least at one candidate ablation location. Method 300 may further include monitoring 318 an outcome of the candidate ablation procedure. Method 300 may also include adding 320 a data record associated with the candidate ablation procedure to the database. Adding 320 may include adding a data element associated with the outcome of the candidate ablation procedure to the data record associated with the candidate ablation procedure. Method 300 may still further include updating 322 the algorithm based upon the data record associated with the candidate ablation procedure.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method of determining a candidate ablation location using historical ablation data, the method comprising:
generating a database including a plurality of ablation records, each ablation record of the plurality of ablation records associated with a corresponding ablation procedure;
generating a set of probability parameters associated with different types of conditions and different types of patients, and describing each ablation record of the plurality of ablation records;
developing, using a regression analysis, an algorithm based upon the sets of probability parameters for the plurality of ablation records; and
for a candidate ablation procedure:
receiving a plurality of patient parameters associated with a patient receiving the candidate ablation procedure;
determining at least one candidate condition associated with the patient and a respective probability associated with each candidate condition;
applying the algorithm to determine at least one candidate ablation location and a probability that ablating in the at least one candidate ablation location will be successful based upon the respective probabilities associated with the at least one candidate condition; and displaying the at least one candidate ablation location on a visual interface of a cardiac mapping system.

2. The method of claim 1 further comprising:
performing the candidate ablation procedure at least at one candidate ablation location; and
adding a data record associated with the candidate ablation procedure to the database.

3. The method of claim 2 further comprising:
monitoring an outcome of the candidate ablation procedure; and
adding a data element associated with the outcome of the candidate ablation procedure to the data record associated with the candidate ablation procedure.

4. The method of claim 2 further comprising:
determining an ablation practitioner that performed the ablation procedure; and
determining whether the ablation practitioner meets at least one expert criterion,
wherein adding a data record associated with the candidate ablation procedure to the database comprises only adding the data record to the database when the ablation practitioner meets the at least one expert criterion.

5. The method of claim 2 further comprising updating the algorithm based upon the data record associated with the candidate ablation procedure.

6. The method of claim 1, wherein generating a database including a plurality of ablation records comprises generating a subset of the plurality of ablation records based upon published data of the corresponding ablation procedures.

7. The method of claim 1, wherein generating a database including a plurality of ablation records comprises generating a subset of the plurality of ablation records based upon historical ablation procedures performed by one or more ablation practitioners who meet at least one expert criterion.

8. The method of claim 1, wherein displaying the at least one candidate ablation location on a visual interface comprises adding at least one visual indicator of a corresponding ablation location onto a map of the cardiac mapping system.

9. The method of claim 8, wherein adding at least one visual indicator comprises adding at least one color to the map to form a probability map identifying the at least one candidate ablation location.

10. The method of claim 8, wherein adding at least one visual indicator comprises adding at least one probability indicator to a respective location on the map corresponding to the at least one candidate ablation location.

11. The method of claim 1, wherein receiving a plurality of patient parameters associated with a patient receiving the candidate ablation procedure comprises receiving at least one of a patient age, a patient gender, a patient weight, one or more known patient conditions, and one or more known patient symptoms.

12. The method of claim 1, wherein generating a database including a plurality of ablation records comprises generating the database including the plurality of ablation records, wherein each ablation record identifies a condition and an ablation location associated with the corresponding ablation procedure.

13. The method of claim 1, wherein displaying the at least one candidate ablation location on a visual interface comprises:
associating each at least one candidate ablation location with a corresponding point on an ablation map of the ablation system; and adding at least one visual indicator onto each point on the ablation map associated with each at least one candidate ablation location.

14. A cardiac mapping system comprising:
a database;
a display device; and
a processing apparatus in communication with the database and the display device, the processing apparatus configured to:
populate the database with a plurality of ablation records, each ablation record of the plurality of ablation records associated with a corresponding ablation procedure;
generate a set of probability parameters associated with different types of conditions and different types of patients, and describing each ablation record of the plurality of ablation records;
develop, using a regression analysis, an algorithm based upon the sets of probability parameters for the plurality of ablation records; and
for a candidate ablation procedure:
receive a plurality of patient parameters associated with a patient receiving the candidate ablation procedure;
determine at least one candidate condition associated with the patient and a respective probability associated with each candidate condition;
apply the algorithm to determine at least one candidate ablation location and a probability that ablating in the at least one candidate ablation location will be successful based upon the respective probabilities associated with the at least one candidate condition; and
display the at least one candidate ablation location on the display device.

15. The cardiac mapping system of claim 14, wherein the processing apparatus is further configured to add a data record associated with the candidate ablation procedure to the database after the candidate ablation procedure is performed.

16. The cardiac mapping system of claim 15, wherein the processing apparatus is further configured to:
receive an indication of an outcome of the candidate ablation procedure;
add a data element associated with the outcome of the candidate ablation procedure to the data record associated with the candidate ablation procedure; and
update the algorithm based upon the data record associated with the candidate ablation procedure.

17. The cardiac mapping system of claim 14, wherein the processing apparatus is further configured to add at least one of a visual indicator of a corresponding ablation location and a probability indicator onto a map displayed on the display device.

18. At least one non-transitory computer-readable storage medium having computer-executable instructions embodied thereon, wherein when executed by at least one processor in communication with a database and a display device, the computer-executable instructions cause the at least one processor to:
populate the database with a plurality of ablation records, each ablation record of the plurality of ablation records associated with a corresponding ablation procedure;
generate a set of probability parameters associated with different types of conditions and different types of patients, and describing each ablation record of the plurality of ablation records;

develop, using a regression analysis, an algorithm based upon the sets of probability parameters for the plurality of ablation records; and for a candidate ablation procedure:
receive a plurality of patient parameters associated with a patient receiving the candidate ablation procedure;
determine at least one candidate condition associated with the patient and a respective probability associated with each candidate condition;
apply the algorithm to determine at least one candidate ablation location and a probability that ablating in the at least one candidate ablation location will be successful based upon the respective probabilities associated with the at least one candidate condition; and
display the at least one candidate ablation location on the display device.

19. The non-transitory computer-readable storage medium of claim 18, wherein the computer-executable instructions further cause the at least one processor to add at least one visual indicator of a corresponding ablation location onto a map displayed on the display device.

20. The non-transitory computer-readable storage medium of claim 19, wherein the computer-executable instructions further cause the at least one processor to add at least one probability indicator to a respective location on the map corresponding to the at least one candidate ablation location.

* * * * *